US00PP15974P3

(12) United States Plant Patent
Hofmann

(10) Patent No.: US PP15,974 P3
(45) Date of Patent: Sep. 20, 2005

(54) **NEW GUINEA *IMPATIENS* PLANT NAMED 'FISUPNIC PINKEYE'**

(50) Latin Name: *Impatiens hawkeri*
Varietal Denomination: Fisupnic Pinkeye

(75) Inventor: Birgit C. Hofmann, Bendorf (DE)

(73) Assignee: Florfis AG (CH)

( * ) Notice: Subject to any disclaimer, the term of this patent is extended or adjusted under 35 U.S.C. 154(b) by 43 days.

(21) Appl. No.: 10/829,349

(22) Filed: Apr. 22, 2004

(65) Prior Publication Data

US 2004/0237159 P1 Nov. 25, 2004

(30) Foreign Application Priority Data

Apr. 29, 2003 (CA) ..... 03-3588

(51) Int. Cl.[7] ..... A01H 5/00
(52) U.S. Cl. ..... Plt./318
(58) Field of Search ..... Plt./318

*Primary Examiner*—Kent Bell
(74) *Attorney, Agent, or Firm*—Foley & Lardner, LLP

(57) ABSTRACT

A new and distinct cultivar of New Guinea *Impatiens* plant named 'Fisupnic Pinkeye', and particularly characterized by the combined features of light pink flowers with purple eyes; very large, round, mostly flat flowers; uniform, medium green foliage; vigorous growth, and tall, upright, bushy plant habit; and medium flowering response.

1 Drawing Sheet

Genus and species of the plant claimed: *Impatiens hawkeri*.

Variety denomination: 'Fisupnic Pinkeye'.

BACKGROUND OF THE INVENTION

The present invention comprises a new and distinct cultivar of New Guinea *Impatiens* plant, botanically known as *Impatiens hawkeri*, and hereinafter referred to by the cultivar name 'Fisupnic Pinkeye'.

'Fisupnic Pinkeye' is a product of a planned breeding program and originated from a hybridization made by the inventor, Birgit C. Hofmann, in a controlled breeding program in Hillscheid, Germany, in the summer of 2000.

The female parent was the variety 'Fisimp 102' (U.S. Plant Pat. No. 13,700), which is characterized by uniform, orange-red flowers, medium green foliage, and fairly tall plant habit. The male parent was the variety 'Fisnics Scarlet Blush' (U.S. Plant Pat. No. 13,227), having scarlet colored flowers with a purple eye, dark green foliage, and medium sized, compact plant habit.

'Fisupnic Pinkeye' was discovered and selected as one flowering plant within the progeny of the stated cross by the inventor in April 2001 in a controlled environment in Galdar, Gran Canaria, Spain.

The first act of asexual reproduction of 'Fisupnic Pinkeye' was accomplished when vegetative cuttings were taken from the initial selection in July, 2001 in a greenhouse in Galdar, Gran Canaria, Spain, by, or under the supervision of the inventor.

Horticultural examination of plants grown from these cuttings initiated in spring, 2002 in Hillscheid, Germany, and continuing thereafter, has demonstrated that the combination of characteristics as herein disclosed for 'Fisupnic Pinkeye' are firmly fixed and are retained through successive generations of asexual reproduction. The new cultivar reproduces true to type.

'Fisupnic Pinkeye' has not been observed under all possible environmental conditions. The phenotype may vary significantly with variations in environment such as temperature, light intensity and day length, without, however, any variation in genotype. The following observations, measurements, and comparisons describe plants grown in Hillscheid, Federal Republic of Germany, under green house conditions which approximate those generally used in commercial practice.

BRIEF SUMMARY OF THE INVENTION

The following traits have been repeatedly observed and are determined to be basic characteristics of 'Fisupnic Pinkeye', which in combination distinguish this *impatiens* as a new and distinct cultivar:

1. Light pink flowers with purple eyes;
2. Very large, round, mostly flat flowers;
3. Uniform, medium green foliage;
4. Vigorous growth, and tall, upright, bushy plant habit; and
5. Medium flowering response.

Of the many commercial cultivars known to the inventor, the most similar in comparison to 'Fisupnic Pinkeye' is the patented variety 'Fisnics Pink' (U.S. Plant Pat. No. 13,228), and 'Fisnics Light Pink' (U.S. Plant Pat. No. 13,579).

In comparison to 'Fisnics Pink', 'Fisupnic Pinkeye' has a lighter main flower color, larger flowers, and much taller plant habit.

In comparison to 'Fisnics Light Pink' 'Fisupnic Pinkeye' has larger flowers, with a less bluish color, and distinctly taller growth habit.

BRIEF DESCRIPTION OF THE DRAWING

The accompanying photographic drawing shows typical flower and foliage characteristics of 'Fisupnic Pinkeye' with colors being as true as possible with illustrations of this type.

The photographic drawing shows a side view of a typical flowering plant of 'Fisupnic Pinkeye'.

DETAILED BOTANICAL DESCRIPTION

In the following description color references are made to The Royal Horticultural Society Colour Chart (R.H.S.). The color values were determined indoors from plants growing in a greenhouse in May 2003, in Hillscheid, Germany.

The description is based on plants which were planted as rooted cuttings in 12 cm pots in late February and then grown in the greenhouse at a minimum temperature of 16° C. Most observations and measurements were made after the beginning of flowering in mid May, when the plants were about 12 weeks old.

PLANT

General appearance and form:

*Plant habit.*—Tall, round, and well-branched; growth is indeterminate, though weak after flowering begins.

*Height.*—23.5 cm.

*Width.*—34.5 cm.

*Number of branches.*—12.

*Length of branches.*—20–22 cm.

*Internode length.*—5.5–6.5 cm.

*Diameter of branches.*—6–7 mm.

*Stem color.*—Reddish-brown, RHS 181 C.

*Propagation.*—Terminal tips for cuttings.

*Rooting.*—Roots initiate in about 18 days at 22° C., from sticking to transplanting.

*Cultivation time.*—It takes about 10 weeks to grow a marketable flowering plant in a 12 cm pot.

Foliage:

*Leaf arrangement.*—Primarily in whorls.

*Shape of leaf.*—Elliptic, with acute base and acute to acuminate tip, surface glossy and somewhat rugose.

*Margin.*—Slightly serrated, ciliated.

*Leaf length.*—12.3 cm.

*Leaf width.*—3.9 cm.

*Upper surface, main color.*—Medium green, uniform, no variegation mature leaves about RHS 137 A young leaves RHS 137 B.

*Veins on upper surface color.*—Pale green, RHS 145 B.

*Lower surface color.*—Light green, about RHS 138 B (both young and mature leaves).

*Veins on lower surface color.*—RHS 51 B.

*Petiole color.*—Upper side dark-red, RHS 51 B; lower side RHS 51 C.

*Petiole size.*—1.5–3.0 cm in length; 3 mm in diameter.

INFLORESCENCE

*Flowering response.*—9–10 weeks after planting of rooted cuttings.

*Flowering season.*—Generally indeterminate, mainly from March to October, depending on light intensity.

Flower:

*Number of flowers per node.*—5–7, in various stages of development.

*Form of corolla.*—Single-type, 5 petals.

*Shape of corolla.*—Very large, nearly round, with the petals overlapping, almost flat, though often somewhat wavy margins.

*Size of corolla.*—Average length: 82 mm. Average width: 80 mm.

Shape of petals: Cordate, slightly lobed at the top end, may be slightly folded. Top petal: 36 mm long, 60 mm wide. Lateral petals: 38 mm long, 40 mm wide. Lower petals: 38 mm long, 44 mm wide.

*Texture.*—Smooth, velvety.

*Aspect.*—Flat or somewhat wavy.

*Color (general tonality from a distance of three meters).*—Bluish-pink, of somewhat variable intensity, with purple center.

*Color of upper surface.*—Light pink RHS 52 C to 52 D, intensity somewhat variable; at the base of the upper petal lavender infused, RHS 72 C.

*Color of eye zone.*—Red-purple, RHS N 57 B.

*Color of lower surface.*—RHS 52 D.

*Spur.*—Downwardly curved, 55 mm long; 3 mm in diameter at the flower end, dark red in color, RHS 53 A.

*Peduncle color.*—Brown, RHS 184 B to 184 C.

*Peduncle length.*—63 mm.

*Flower bud.*—Ovoid in shape; 22 mm in length; 16 mm in width; color approximately RHS 52 C.

Reproductive organs:

*Stamens.*—5 in number, fused, upper surface color is RHS N57 C.

*Anthers.*—Fused, hooded.

*Pollen.*—Whitish-yellow, about RHS 8 D.

*Style and stigma.*—Five in number, very short, color about RHS 150 D.

*Ovary.*—5-celled, 5 mm long, surface color green, RHS 141 B.

Disease/pest resistance/susceptibility: No observation made to date.

I claim:

1. A new and distinct cultivar of New Guinea *Impatiens* plant named 'Fisupnic Pinkeye', as described and illustrated herein.

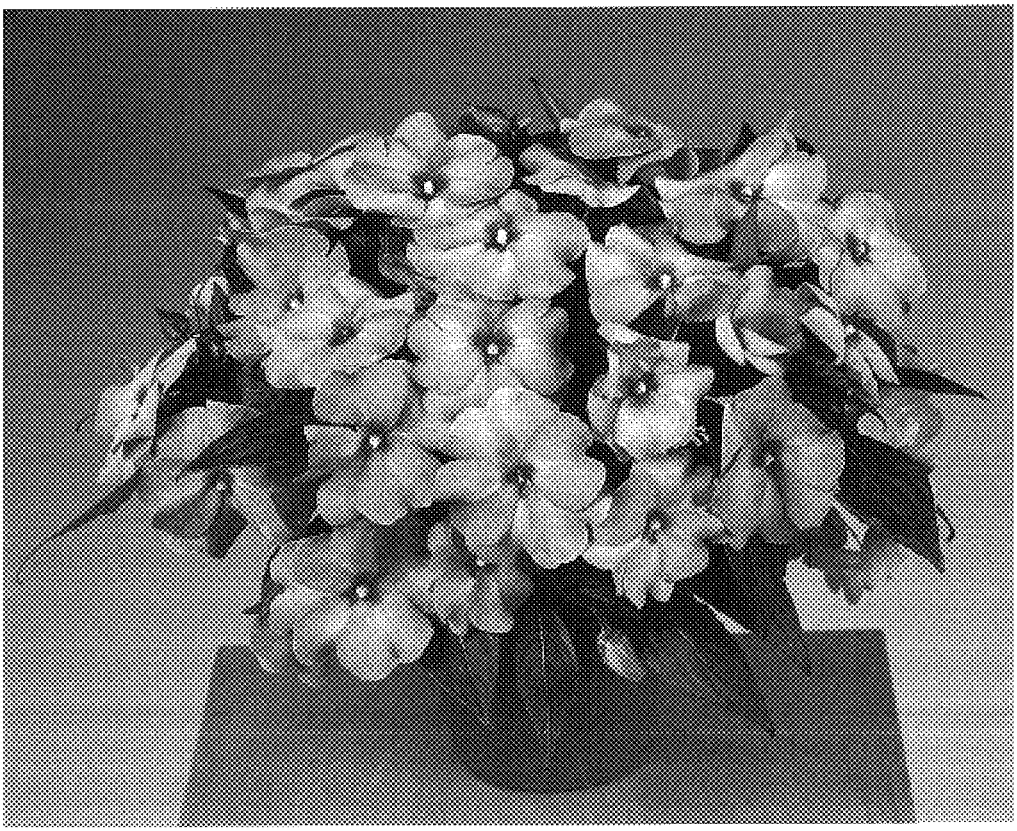

* * * * *